US011328697B1

(12) United States Patent
Stewart et al.

(10) Patent No.: US 11,328,697 B1
(45) Date of Patent: May 10, 2022

(54) PROTECTIVE DEVICE MINIMIZING DISPERSION OF AIRBORNE PATHOGENS FROM WIND INSTRUMENTS

(71) Applicants: David B Stewart, Cranbury, NJ (US); Frances M Stewart, Cranbury, NJ (US)

(72) Inventors: David B Stewart, Cranbury, NJ (US); Frances M Stewart, Cranbury, NJ (US)

( * ) Notice: Subject to any disclaimer, the term of this patent is extended or adjusted under 35 U.S.C. 154(b) by 0 days.

(21) Appl. No.: 17/224,111

(22) Filed: Apr. 6, 2021

(51) Int. Cl.
*G10D 9/00* (2020.01)
*A61L 9/014* (2006.01)
*G10D 7/10* (2006.01)
*G10G 7/00* (2006.01)

(52) U.S. Cl.
CPC ............... *G10D 9/00* (2013.01); *A61L 9/014* (2013.01); *G10D 7/10* (2013.01); *G10G 7/00* (2013.01); *A61L 2209/14* (2013.01); *A61L 2209/15* (2013.01)

(58) Field of Classification Search
CPC .. G10D 9/00; G10D 7/10; A61L 9/014; A61L 2209/14; A61L 2209/15; G10G 7/00
See application file for complete search history.

(56) References Cited

U.S. PATENT DOCUMENTS

2021/0329995 A1\* 10/2021 Dietz .................... A62B 23/02

OTHER PUBLICATIONS

Musicians Improvise Masks for Wind Instruments to Keep the Band Together | Kaiser Health News (khn.org); UNGAR, Oct. 16, 2020 https://khn.org/news/musicians-improvise-masks-for-wind-instruments-covid-protection/ (Year: 2020).\*

\* cited by examiner

*Primary Examiner* — Kimberly R Lockett
(74) *Attorney, Agent, or Firm* — Henry I. Schanzer

(57) ABSTRACT

Apparatus attached to the flared open end of a wind instrument includes one or more layers of particle filtering materials for preventing the dispersion of pathogens from the wind instrument while enabling sound transmission with little muffling and distortion, and minimal resistance for the musician.

9 Claims, 6 Drawing Sheets

PROTECTIVE DEVICE MINIMIZING DISPERSION OF AIRBORNE PATHOGENS FROM WIND INSTRUMENTS

This invention claims priority based on a U.S. provisional application Ser. No. 63/039,327 filed 15 Jun. 2020 titled PROTECTIVE DEVICE MINIMIZING DISPERSION OF AIRBORNE PATHOGENS FROM WIND INSTRUMENTS whose teachings are incorporated herein by reference.

BACKGROUND OF THE INVENTION

A microorganism, or microbe, is a microscopic organism, which may exist in its single-celled form or in a colony of cells. Microbes are important in human culture and health in many ways, serving to ferment foods, treat sewage, produce fuel, enzymes and other bioactive compounds. They are essential tools in biology as model organisms and have been put to use in biological warfare and bioterrorism. They are a vital component of fertile soils. In the human body microorganisms make up the human microbiota including the essential gut flora.

They are the pathogens responsible for many infectious diseases and as such are the target of hygiene measures. The latter group of microbes can be responsible for the illness and often death resulting from seasonal influenza (the "flu") or widespread virus outbreaks (e.g., pandemics).

Many microbes are dispersed in aerosol form during human respiration, coughing or sneezing. An aerosol (abbreviation of "aero-solution") is a suspension of fine solid particles or liquid droplets in air or another gas. Aerosols can be natural or anthropogenic." Microbe-laden aerosols are produced with normal breathing (respiration), talking and singing to differing degrees. Studies have shown the following:

- Coughing and sneezing create relatively large droplets that settle to the ground relatively quickly.
- Speaking and singing create aerosols which can hang in the air longer and travel farther than the large droplets.
- Talking produces about 10× more aerosols than breathing.
- Singing produces about 60× more aerosols than breathing.
- Blowing on a wind instrument produces as much as 100× aerosols than breathing.

In times of a microbial-caused pandemic, it is highly problematic to play wind instruments (e.g., brass instruments, woodwind instruments) since as noted above they tend to allow the production and dispersal of a large amount of droplets containing pathogens.

As discussed above and as is known, wind instrument playing requires an intensive exchange of air in the lungs and respiratory tract with sometimes high air pressures. It is to be assumed that the release of the breathing air into the environment during playing can lead to pathogen containing aerosols. In addition, playing wind instruments causes condensation of the exhaled air in the instrument, which is to be regarded as another potentially pathogen-spreading material.

Applicants' invention is directed to apparatus for reducing the release into the air of pathogen containing aerosols when playing wind instruments.

SUMMARY OF THE INVENTION

This invention relates to pathogen reducing devices attached to a musical instrument for reducing pathogen dispersion emanating from the musical instrument into the surrounding air, external to the instrument. The invention is directed to reducing dispersion from wind musical instruments (e.g., trumpet, trombone, tuba) and like structures. A device embodying the invention includes apparatus mounted to and about the flared open end of a wind instrument; with the apparatus having a greater surface area than the cross sectional area of the flared open end to limit the dispersion of pathogens while enabling the passage of sound.

Note: the flared end of wind instrument is also referred to herein as the "bell" of the wind instrument. For musical instruments with small bells (e.g., trumpet), the protective device can be secured in a way that increases the area of the protective device relative to the area across the bell, so that the resistance to air flow is reduced and the average velocity at which the air moves through and exits the protective device. For example, the protective device can be in the rough form of a dome or cone or be cylindrical, such that the amount of pathogen-reducing material is increased from that of a shield consisting only of material stretched taut across the bell. The filtering and support material for the increased-surface area device can be supported with a lightweight structure consisting of plastic or metal wire frames.

The pathogen dispersion reducing devices (also referred to herein as "shield") include one or more layers of material that limit the quantity or volume of pathogens that can pass through the layers and be projected from the wind instrument. The layers of material may be mounted on or attached to a support structure or frame, which can be dome like or cylindrical, attachable to the flared end of the wind instrument for reducing the pathogens that can be dispersed into the air during the playing of the wind instrument while providing greater surface area and volume for sound propagation.

The COVID-19 virus prevalent in year 2020 is approximately 0.125 Micron, or 125 nanometers in diameter. It often travels in biological aerosols from coughing and sneezing which range in size from 0.5-3 micron. Typically, people wear surgical masks or N95 or KN95 rated masks to prevent themselves and others from being exposed to viruses like COVID-19. Certain face masks (e.g., the N95 or KN95) capture 95% of particles down to 0.3 micron. This means that 5% of the pathogens of this size still get through the protection.

Many air filtration systems use High Efficiency Particulate Air ("HEPA") filters which can capture microbes, dust, and particulates down to 0.3 Micron. The U.S. Department of Energy first termed HEPA as a filtering specification for suppliers of filtration products based on how effective they were at particle removal. HEPA filters consist of a complex mix of filaments and fibers that carry a static charge which lures various microbes and particles like a magnet. HEPA air purifiers, in contrast to N95 and KN95 rated face masks, are 99.97% effective at 0.3 Micron and are much more efficient than face masks.

A wind instrument pathogen protective device (or "shield" or "filter") embodying the invention may include the same type of material(s) used in surgical masks or HEPA filters. The pathogen protecting device is shaped to fit about the "bell" of the wind instrument and to include means for securing it to the wind instrument.

The pathogen protective device may also include an additional overlying layer such as a breathable fabric (e.g., cotton) to protect the underlying layer against excessive wear and still provide additional filtering. Typically, the overlying layer will be of a material which is less expensive than the surgical mask or HEPA filter material.

BRIEF DESCRIPTION OF THE DRAWINGS

In the accompanying drawings, which are not drawn to scale, like reference denote like components.

DETAILED DESCRIPTION OF THE FIGURES

Figure 1:
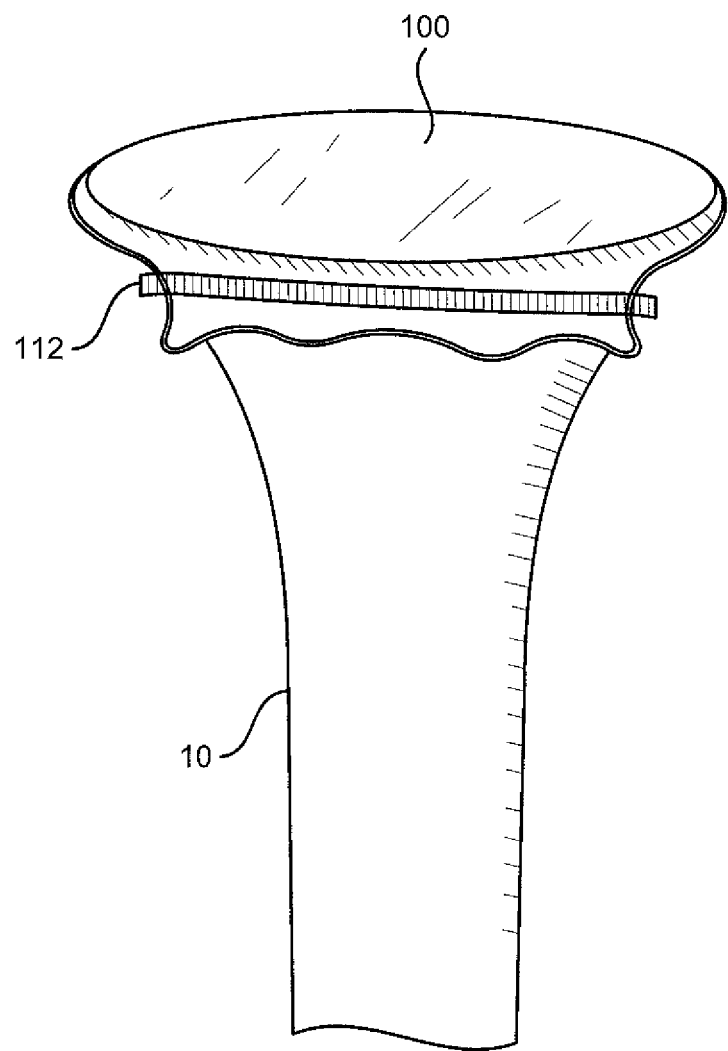
FIG. 1 is an isometric view of a "protective shield" (i.e., shield to reduce quantity of pathogens dispersed from wind instrument) embodying the invention mounted across the bell (mouth) of a wind instrument.
Figure 2:
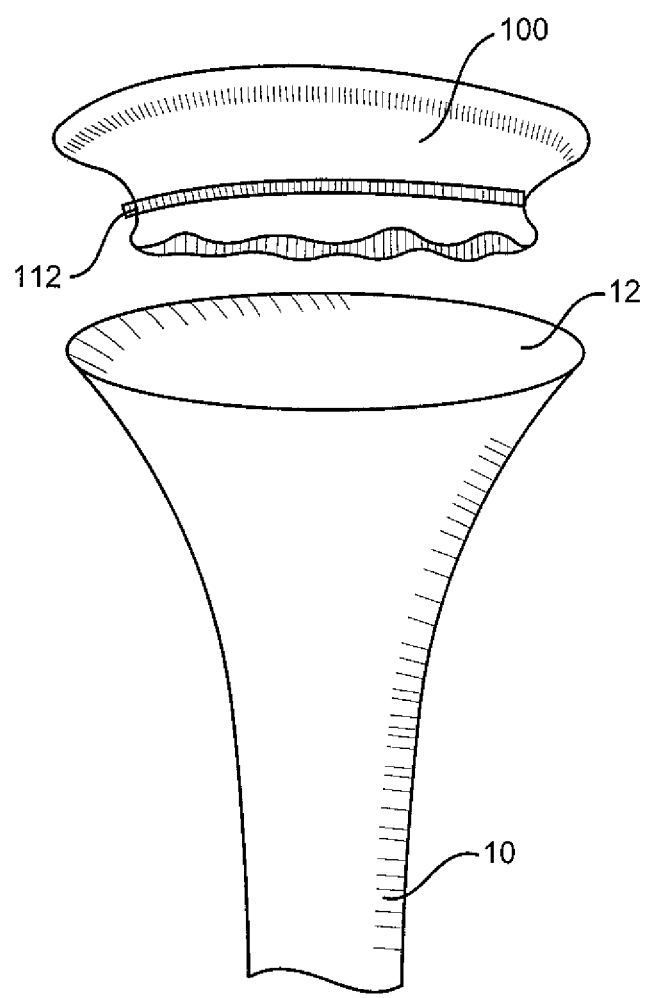
FIG. 2 is an exploded view of the protective shield and the bell portion of the wind instrument of FIG. 1.
Figure 3:
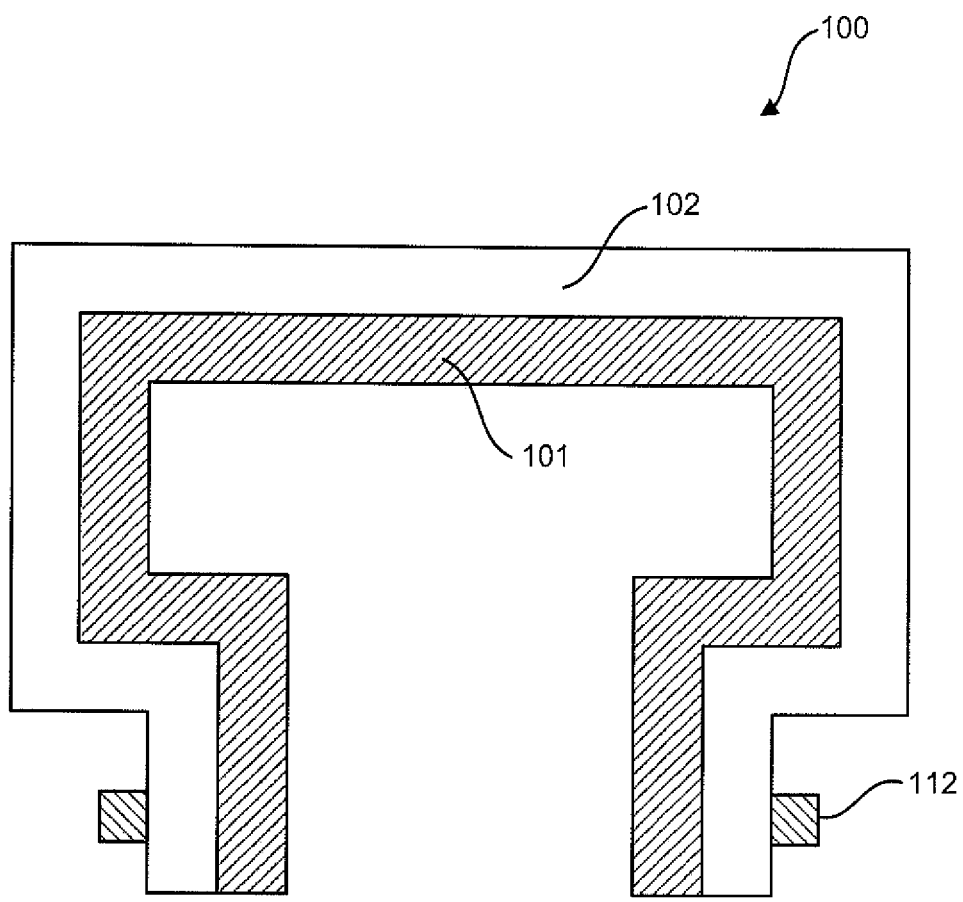
FIG. 3 is an idealized simplified cross-sectional view of a protective shield embodying the invention.

Referring to FIGS. 1 and 2, there is shown an isometric view of a musical wind instrument 10 with a shield 100 mounted exteriorly across the bell 12 of the instrument 10. The shield 100 is secured to the wind instrument by means of a securing element 112. FIG. 3 is a highly simplified cross-sectional view of the shield 100 and FIG. 3A is a highly simplified cross-sectional view of the shield 100 shown mounted on the flared end of an instrument 10.

The shield 100 is shown formed of two layers. A first layer 101 and an overlying layer 102. The layer 101 may be formed of materials similar to those used to form surgical masks and/or to meet the standards of HEPA filters. HEPA (high efficiency particulate air) filters are also known as high-efficiency particulate absorbing and high-efficiency particulate arrestance filters and function as an efficiency standard of air filter. However, it should be appreciated that even cotton layers can be beneficial. So, any suitable filtering material can be used for layer 101.

Layer 101 is the main layer which functions to reduce the transmission of pathogens form the wind instrument 10. The second overlying layer 102 is made of a breathable fabric to protect the underlying layer 101 from being torn or damaged. Layers 101 and 102 can be permanently affixed to each other or selectively attached to each other. Protective layer 102 can also include a suitable filtering material.

Alternatively, layers 101 and 102 can just be mounted one on top of the other. The layers 101 and 102 are secured together and to the instrument 10 via an adjustable securing element 112 at a selected distance below the outer lip of the instrument 10, as shown in FIG. 1. Alternatively, the layer 101 may be inserted into a pocket formed within an overlying, and surrounding, layer 102 to form shield 100. As shown in FIGS. 3 and 3A the surface area of shield 100, overlying the flared opening of the wind instrument, is significantly greater than the cross-surface area of the bell 12 of the wind instrument (i.e., the shield is not taut across the bell of the instrument). As is evident from the description above, Applicants' invention is directed to a simple but effective means for preventing or at least minimizing the dispersion of pathogens from the wind instrument while enabling sound transmission with little muffling and distortion.

In practicing the invention, the inner layer 101 may be formed of one or more layers of pathogen-reducing or blocking or filtering material.

In practicing the invention, the exterior, overlying or outer layer 102 may be formed of one or more layers of protective cloth material.

The shield 100 comprised of layers 101 and 102 is designed to reduce muffling and distortion of the sound emanating from the instrument. The bottom portion of layers 101 and 102, as shown in the Figures, may be pulled tight around the narrowing section of the instrument's bell by a securing element 112 designed to secure the shield to and around the narrowing section of bell 12. The securing element 112 may be an elastic, fabric drawstring, Velcro-type material, or any other material that can pull the open end of the shield tight against the bell.

Shield (filter) material could be sandwiched between inner and outer layers of support material. Shield material could be in a "pocket" such that it can be replaced, and the protective support layers can be reused.

Protective and shielding layers can be sewn together, such that the device is disposable once the shield material is saturated and is no longer effective, or the pocket arrangement could be used.

As is evident from the description above, Applicants' invention is directed to a simple but effective means for preventing or minimizing the dispersion of pathogens from the wind instrument while enabling sound transmission with little muffling and distortion.

Figure 4:
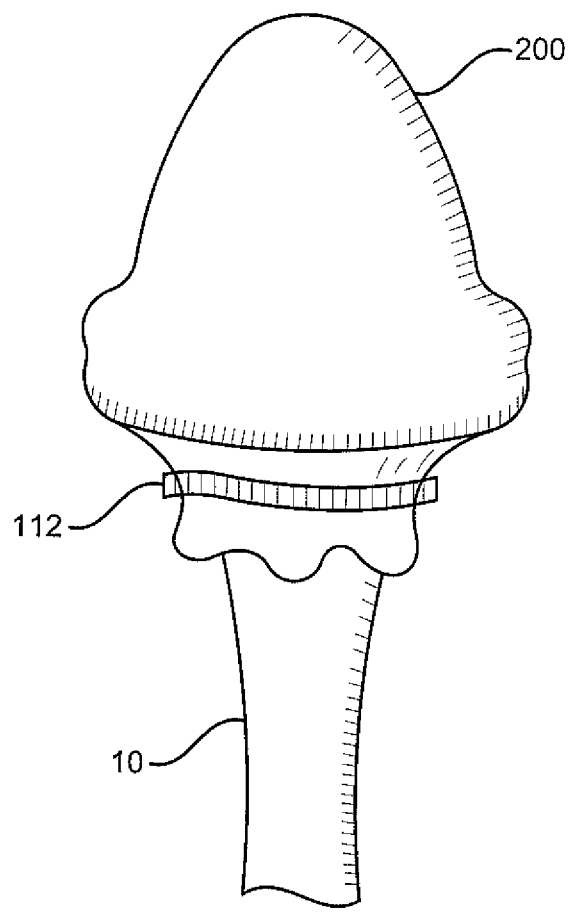
FIG. 4 is an isometric view of another "protective shield" embodying the invention mounted across the bell (mouth) of a wind instrument.
Figure 5:
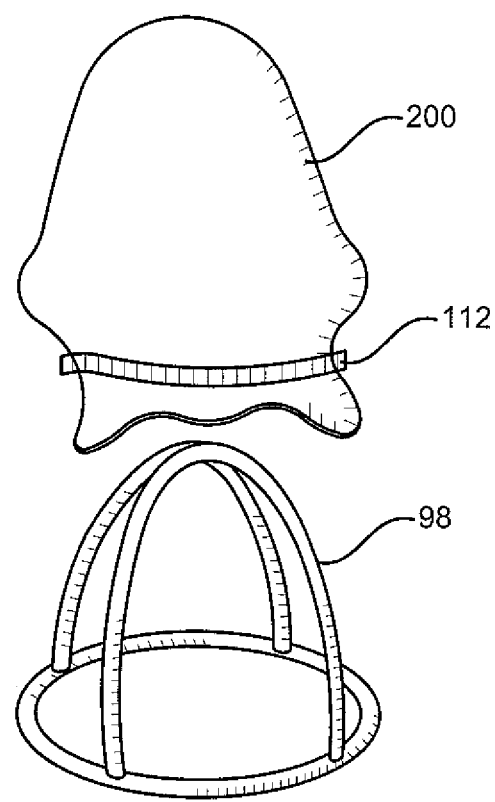
FIG. 5 is an exploded view of the protective shield and the bell portion of the wind instrument of FIG. 4.

Referring to FIGS. 4 and 5, there is shown a dome shaped shield 200 which includes a frame structure 98 in addition to the layers 101 and 102 of the shield 100. In essence, shield 200 differs from the shield 100 in that a support structure 98 is provided which pushes the pathogenic blocking materials away from the bell, in order to increase the surface area of the shield and thereby decrease the resistance to air flow.

Figure 6:
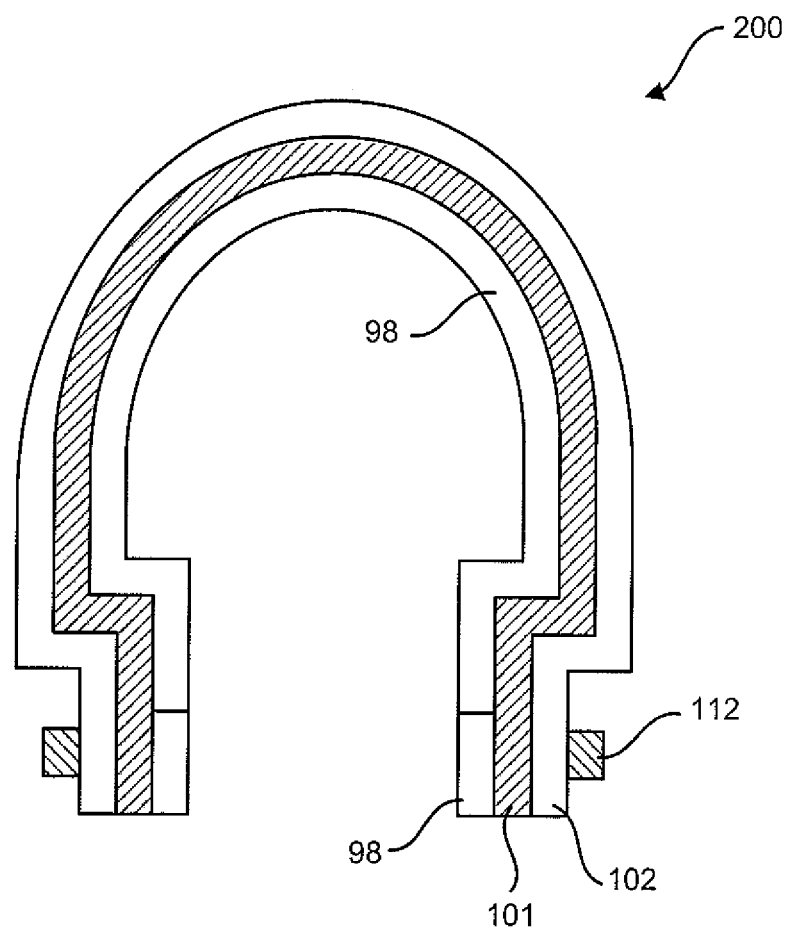
FIG. 6 is an idealized cross-sectional view of the protective shield embodying the invention shown in FIGS. 4 and 5.

FIG. 6 is a highly simplified cross sectional diagram showing the three layers 98, 101 and 102. As shown in FIGS. 4 and 5, the shield 200 is mounted about the outer periphery of the instrument's bell and is secured to the instrument via an adjustable securing means 112. The most inner layer 98 is designed to increase the surface area across and through which the sound output of the instrument can propagate. Frame 98 can be mounted, or attached, at its lower ends to the outer rim of the instrument's bell 12 or just below the outer rim. Structure 98 may be a stiff or a semi-stiff support structure which keeps layers 101 and 102 away from being right on top of the bell's opening. This increases the surface area of the shield and thereby decrease the resistance to air flow. The structure 98 can be made of plastic, metal, or some other material that is lightweight and strong enough to support the shielding materials, 101, 102. The support structure 98 can include wires or tubes which can be attached to a "rim" that is approximately of the same diameter as the instrument's bell. The support structure 98 can rest on the rim of the bell 12 and be held in place by the pressure applied by the securing element 112, which can be an elastic band or any type of known securing string or Velcro strip. Alternatively, the securing means may be small clips that are attached to or a part of the shield support structure 98 and attach to the rim of the bell 12.

Structure 98 and layers 101 and 102 can be permanently affixed to each other or selectively attached to each other. Alternatively, layers 98, 101, and 102 can just be mounted one on top of the other.

The support structure 98 can be made of plastic, metal, or some other material that is lightweight and strong enough to support the shielding material. The "wires" of the support structure can be attached to a "rim" that is approximately of the same diameter as that of the instrument's.

Embodiments of the invention may include the following:
1. Multiple layers of shield or filter material.
2. Different layers of shield or filter material which can be separated using a thin cloth material or semi-stiff frame such that the effectiveness of the multiple layers is increased. That is, each layer slows the velocity of the aerosol droplets, thereby increasing the chance that they are trapped by the next shield layer.

As noted above, Applicants' invention is directed to a simple but effective means for preventing the dispersion of pathogens from a wind instrument while enabling sound transmission with little muffling and distortion.

What is claimed is:

1. In combination with a wind instrument having a flared open end from which pathogens may be emitted, apparatus for reducing emission of pathogens from the flared open end of the wind instrument comprising:
   a support structure attachable to the flared open end of the instrument, said support structure shaped to span the flared open end of the wind instrument and to extend outwardly therefrom for a predetermined distance; and
   a layer of material draped over the support structure and secured to the flared open end of the wind instrument; wherein the combination of said support structure and said layer of material decreases the emission of pathogens emitted from the flared end while providing a greater area and volume for the propagation of sound from the wind instrument.

2. Apparatus as claimed in claim 1, wherein said layer of material includes materials similar to those used in surgical masks or HEPA filters.

3. Apparatus as claimed in claim 1, wherein the layer of material draped over the support structure includes a first layer of material used in surgical masks or HEPA filters and a second layer, overlying the first layer, for providing protection for the first layer.

4. Apparatus as claimed in claim 1, wherein said support structure is a dome-like structure having a base mounted on, or about, the flared open end of the wind instrument.

5. Apparatus as claimed in 4, wherein said layer of material includes a first layer of material used in surgical masks or HEPA filters and a second layer, overlying said first layer, to protect the first layer from being torn or pierced.

6. Apparatus as claimed in claim 5 wherein the dome-like structure and said first and second layers are secured to the wind instrument.

7. In combination with a wind instrument having a flared open end from which pathogens may be emitted, apparatus for reducing emission of pathogens emitted from the flared open end of the wind instrument comprising:
   a support structure attachable to the flared open end of the instrument, said support structure shaped to span the flared open end of the wind instrument and to extend outwardly therefrom for a predetermined distance;
   a layer of material draped over the support structure; and
   means for securing the support structure and the layer of material to the wind instrument so the layer of material overlies the flared open end of the wind instrument; wherein the combination of said support structure and said layer of material decreases the emission of pathogens from the flared end while providing a greater area and volume for the propagation of sound from the wind instrument.

8. Apparatus as claimed in 7, wherein said layer of material includes: (a) a first layer of material used in surgical masks or HEPA filters; and (b) a second layer, overlying said first layer, to protect the first layer from being torn or pierced.

9. Apparatus as claimed in claim 8 wherein said securing means enables the layer of material to be firmly attached to or detached from the wind instrument.

\* \* \* \* \*